US010060839B2

(12) United States Patent
Berberich

(10) Patent No.: US 10,060,839 B2
(45) Date of Patent: Aug. 28, 2018

(54) AUTOMATED EMBEDDING MACHINE, AND METHODS FOR EMBEDDING A HISTOLOGICAL SAMPLE

(71) Applicant: Leica Biosystems Nussloch GmbH, Nussloch (DE)

(72) Inventor: Markus Berberich, Heidelberg (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 0 days.

(21) Appl. No.: 15/499,314

(22) Filed: Apr. 27, 2017

(65) Prior Publication Data

US 2017/0227431 A1 Aug. 10, 2017

Related U.S. Application Data

(62) Division of application No. 14/552,946, filed on Nov. 25, 2014, now Pat. No. 9,671,322.

(30) Foreign Application Priority Data

Dec. 10, 2013 (DE) .................. 10 2013 225 397

(51) Int. Cl.
*G01N 1/36* (2006.01)

(52) U.S. Cl.
CPC .......... *G01N 1/36* (2013.01); *G01N 2001/366* (2013.01)

(58) Field of Classification Search
CPC .......................... G01N 2001/366; G01N 1/36
See application file for complete search history.

(56) References Cited

U.S. PATENT DOCUMENTS

| 5,817,032 | A | 10/1998 | Williamson, IV et al. |
| 7,722,810 | B2 | 5/2010 | Allen et al. |
| 8,052,928 | B2 | 11/2011 | Ulbrich et al. |
| 2009/0210254 | A1 | 8/2009 | Gurney |
| 2010/0151513 | A1 | 6/2010 | Vom et al. |
| 2010/0248301 | A1 | 9/2010 | Ulbrich et al. |
| 2014/0273085 | A1 | 9/2014 | Eckert et al. |

FOREIGN PATENT DOCUMENTS

| EP | 2322938 | 1/2013 |
| WO | 2005037182 A2 | 4/2005 |
| WO | 2009152575 | 12/2009 |
| WO | 2013049564 | 5/2013 |

*Primary Examiner* — Robert B Davis
(74) *Attorney, Agent, or Firm* — Hodgson Russ LLP

(57) ABSTRACT

An automated embedding machine includes at least a conveyor, a pouring station, and a cooling station. The conveyor is embodied and arranged to receive casting molds each having at least one histological sample arranged therein, and to transport them to the pouring station which fills each casting mold with an embedding medium heated to above its melting point, and then to the cooling station which cools the embedding medium of each casting mold to below its melting point. The disclosure furthermore relates to a method for embedding a histological sample.

13 Claims, 2 Drawing Sheets

AUTOMATED EMBEDDING MACHINE, AND METHODS FOR EMBEDDING A HISTOLOGICAL SAMPLE

CROSS REFERENCE TO RELATED APPLICATIONS

Figure 1:
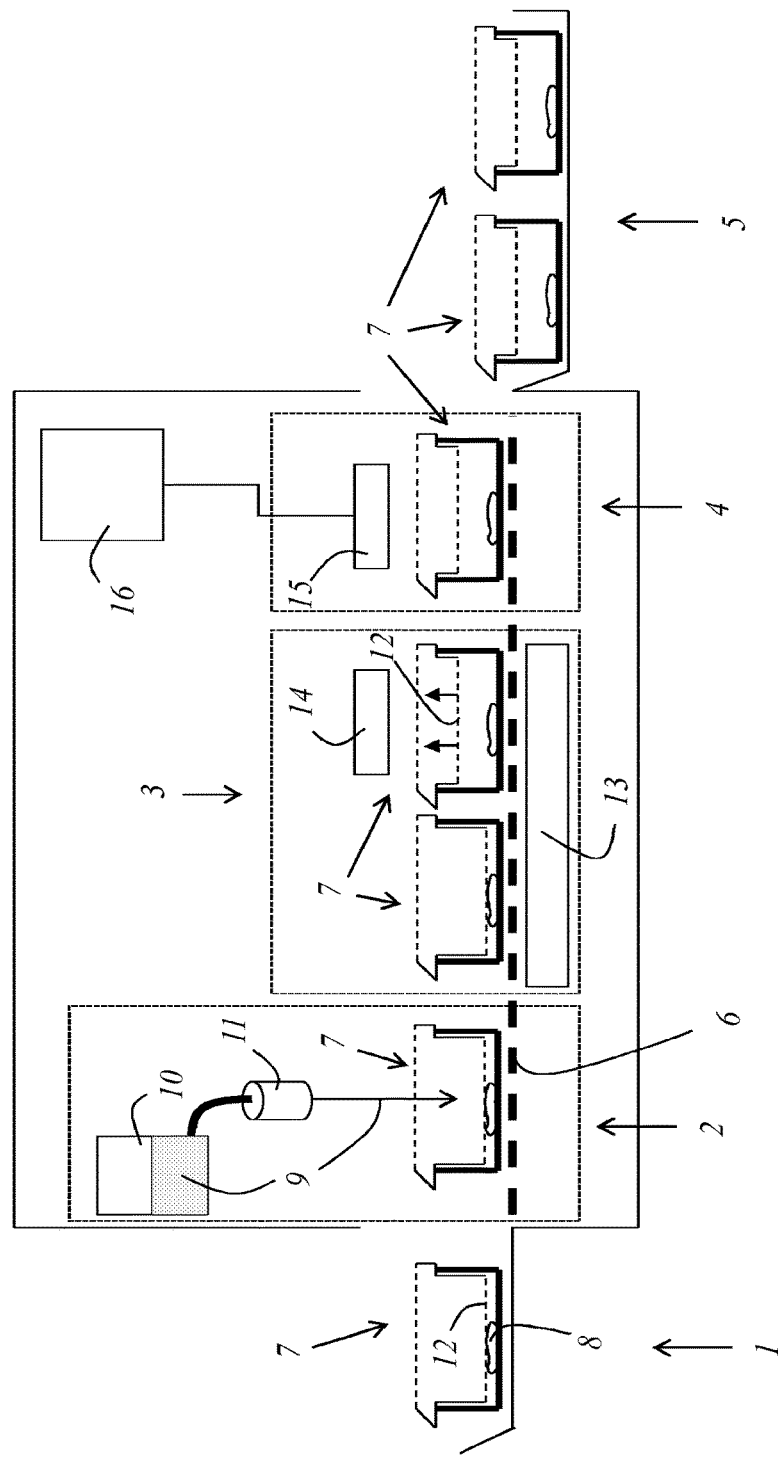

This application is a divisional application of U.S. application Ser. No. 14/552,946 filed Nov. 25, 2014, which claims priority of German patent application number 10 2013 225 397.4 filed Dec. 10, 2013, the entire disclosures of which are incorporated by reference herein.

FIELD OF THE INVENTION

The invention relates to an automated embedding machine.

BACKGROUND OF THE INVENTION

The manner in which a biological tissue sample is to be prepared for histological investigation is known. Firstly the tissue sample is cut to size and introduced into a cassette. The sample is then prepared, using a plurality of chemical treatments, for microscopic investigation. In the context of chemical treatment, firstly the sample is fixed with a fixing medium, the water present in the sample is removed, and optionally further processing steps are completed. At the end of this multi-step process is infiltration of an infiltration medium, usually paraffin, into the sample. The sample is then embedded, usually manually, into an embedding medium, usually paraffin, by means of a molding operation, and the embedded block is connected to the cassette. The cassette serves as a carrier that can be introduced into a corresponding receptacle of a microtome and fastened there.

The result is an embedded block with cassette in which the sample is secured in stationary fashion. After hardening of the embedding medium, the sample can be sectioned with the microtome into individual thin sample sections that, in a subsequent step, can be stained and investigated with a microscope.

EP 2 322 938 B1 discloses an automated machine that is embodied to embed tissue samples onto very special carriers, namely those which are suitable for being sectioned with a microtome together with the embedded sample. The machine comprises multiple immovable holders, each holder being embodied to hold one of the special carriers during the entire embedding operation. Once a carrier filled with a sample has been positioned in a holder, the carrier is filled with an embedding medium that is delivered from a dispenser. The carrier is then cooled by the holder, which in order to implement an additional function is additionally embodied as a cooling unit. During the entire embedding process, each carrier remains in its position defined by the respective holder. The dispenser services all of the plurality of holders.

The concept on which this machine is based disadvantageously requires a complex and malfunction-prone configuration. This relates in particular to the dispenser, which must be able to reach each individual one of the holders so that paraffin heated to above its melting point can be distributed.

SUMMARY OF THE INVENTION

The object of the present invention is to describe an automated embedding machine that can be of simpler and less malfunction-prone configuration.

The object is achieved by an automated embedding machine that comprises at least a conveyor, a pouring station, and a cooling station, the conveyor being embodied and arranged to receive casting molds each having at least one histological sample arranged therein, and to transport them to the pouring station which fills each casting mold with an embedding medium heated to above its melting point, and then to the cooling station which cools the embedding medium of each casting mold to below its melting point.

A further object of the present invention is to provide a method for embedding histological samples, which method can be carried out in simple and reliable fashion, in particular automatically.

This object is achieved by a method that is characterized by the following steps:

a. inserting histological samples into casting molds, at least one histological sample being inserted into one casting mold, b. transferring the casting molds having the samples to a loading station of an automated embedding machine that comprises a conveyor, a pouring station, and a cooling station, c. conveying the transferred casting molds, using the conveyor, to a pouring station that fills each casting mold with an embedding medium heated to above its melting point, and d. conveying the casting molds, filled with the embedding medium, to a cooling station that cools the embedding medium of each casting mold to below its melting point.

The automated embedding machine according to the present invention has the advantage in particular that (in contrast, for example, to the aforementioned machine known from EP 2 322 938 B1) there is no need for the presence of multiple mutually independent positioning systems, namely on the one hand for the casting molds and on the other hand, for example, for a dispenser for delivering the embedding medium. In particular, only a single conveyor needs to be present, so there is no risk of elements of different transport systems colliding with one another, and there is no need to laboriously configure different transport systems in such a way that a collision of individual elements of said systems is avoided.

The automated embedding machine can advantageously comprise at least one further station.

A loading station, into which the casting molds each having at least one histological sample arranged therein are loadable and from which the conveyor receives the casting molds for further transport, can be present, for example, as a further station.

Transfer of the casting molds having the samples to a loading station of an automated embedding machine can be accomplished, for example, in such a way that individual casting molds are transferred sequentially. It is also possible, however, for the casting molds to be transferred in groups. The loading station of the automated embedding machine can be embodied in particular as a loading buffer. This has the advantage that there is no need to wait until the previously loaded casting molds have been received by the conveyor and transported out of the loading station before further casting molds can be loaded into the loading station.

In the particular embodiment, provision is made that a sorting of the loaded casting molds is performed in the loading buffer. This can occur in particular automatically, for example by way of a control apparatus. The sorting can be accomplished, for example, in such a way that, for example, casting molds having samples of the same type are sorted into one group. These can be, for example, samples that are later to be stained in the same manner, or samples that are to be embedded using the same embedding medium (for example, the same grade of wax), or samples of the same tissue type. Alternatively or additionally, it is also possible to sort with respect to one another the casting molds having the samples of a specific patient or of a specific group of patients.

Provision can be made in particular that the casting molds sorted with respect to one another in a group can be embedded in one treatment cycle together or in immediately successive treatment cycles. This has the advantage, for example, that frequent changeovers within the automated embedding machine are avoided, for example when different samples need to be embedded using different grades of wax and/or at different temperatures.

Alternatively or in addition to sorting, a prioritization of individual casting molds, for example of casting molds having samples to be embedded particularly urgently, can occur in the loading buffer, preferably automatically under the control of a control apparatus. For example, a control apparatus can perform a prioritization in such a way that casting molds having particularly urgent samples are forwarded to the subsequent stations before casting molds having samples that are not urgent.

Provision can be made, for example, that a reading apparatus in the loading buffer detects, for example on the basis of a code, in particular a barcode, mounted on the casting mold, the parameters with which embedding is to occur, for example the embedding medium with which the sample of that casting mold is to be embedded and/or the temperature at which embedding is to occur and/or the temperature at which cooling is to occur. Provision can also be made for detecting the priority of a casting mold based on such a code.

Alternatively or additionally, other further stations to which the casting molds are transported by the conveyor can also be present.

In a particular embodiment, the automated embedding machine comprises an unloading station to which the conveyor transports the casting molds having the cooled embedding medium. The user, or a further automated machine, can remove the completed blocks from the unloading station for further processing. It is particularly advantageous if the unloading station is embodied as an unloading buffer. This has the advantage of avoiding formation of a "traffic jam" of completed blocks, which can cause the process of manufacturing further blocks to be halted until the jam has been eliminated. This yields the further advantage that the completed blocks do not need to be removed from the automated embedding machine immediately after they are manufactured.

In the particular embodiment, provision is made that a sorting of the casting molds is performed in the unloading buffer. This can be accomplished in particular automatically, by example under the control of a control apparatus. The sorting can be accomplished, for example, in such a way that, for example, casting molds having samples of the same kind are sorted into one group. These can be, for example, samples that are to be stained in the same manner, or samples that are to be sectioned in a microtome in the same manner, or samples of the same tissue type. Alternatively or additionally, it is also possible to sort with respect to one another in the unloading buffer those casting molds having the samples of a specific patient or of a specific group of patients, so that they can be removed together.

Alternatively or in addition to sorting, a prioritization of individual casting molds, for example of casting molds having samples to be embedded particularly urgently, can occur in the unloading buffer, preferably automatically under the control of a control apparatus. For example, a control apparatus can perform a prioritization in such a way that casting molds having particularly urgent samples can be removed from the unloading buffer before casting molds having samples that are not urgent.

Provision can be made, for example, that a reading apparatus in the unloading buffer detects, for example on the basis of a code, in particular a barcode, mounted on the casting mold, how sorting is to occur or what priority the respective casting mold has.

An identification station, to which the casting molds are conveyed by the conveyor in particular immediately after leaving the cooling station, can be present as a further station. The identification station can comprise an identifier that receives and/or reads off a specific code for each casting mold and/or for the sample present therein and/or for each block that has been produced. For example, a specific barcode that the identifier can read off can be imprinted onto each casting mold. Alternatively, a casting mold can also comprise an RFID chip that permits identification.

In a very particularly advantageous embodiment, the automated embedding machine comprises an information output interface that outputs, for example to a laboratory information system, an information item about an identified casting mold and/or an identified sample and/or an identified block. Alternatively or in addition to an information output to a laboratory information system, for example, a report can also be outputted locally; this can be accomplished, for example, by a printout on paper or by display on a monitor of the automated embedding machine.

The conveyer can be embodied in a very wide variety of ways.

In a particular embodiment the conveyor transports the casting molds in a continuous transport stream along a predefined conveying path. An embodiment of this kind can advantageously be implemented with very little complexity or outlay. In particular, an embodiment in which the conveyor transports the casting molds individually along the predefined transport path permits an overall process that is clear and easy to monitor, and therefore has little susceptibility to malfunction.

The continuous transport stream can proceed in such a way that all the casting molds always have the same transport speed. An embodiment in which the individual casting molds are transported within the continuous transport stream independently of one another and/or at different instantaneous speeds and/or in timed fashion along the predefined conveying path is, however, particularly advantageous.

Provision can also be made that the conveyor transports the casting molds in groups along a predefined conveying path. The casting molds of each group can, for example be respectively secured in a shared holder. An embodiment of this kind has the advantage of a particularly high throughput.

In particular, the conveyor can comprise a transport line and/or a conveyor belt. Alternatively or additionally, the conveyor can advantageously be embodied, for example, as a belt conveyor and/or as a segment conveyor and/or as a roller conveyor and/or as a continuous conveyor.

An embodiment of the automated embedding machine in which the conveying path is identical for all casting molds is particularly simple to implement and particularly unsusceptible to malfunction. It is possible, however, to embody the conveyor in such a way that different casting molds take different conveyor paths, for example if multiple stations of one station type are present and are operated in parallel.

In a particular embodiment that can be embodied in particular as an alternative to implementation of a continuous transport stream, the conveyor comprises a holder for multiple casting molds which is movable relative to the stations, the holder being moved by a control apparatus in such a way that each of the casting molds held by the holder travels successively to each of the stations. For example, an X-Y displacement stage with which the holder can be positioned can be present.

In a particular embodiment the sample is cooled exclusively by the action of cold from one direction, for example from below. This has the advantage, as compared with cooling from all sides, that stress cracks within the paraffin do not occur.

In order to ensure that the sample or samples have, within the block that is to be produced, a favorable alignment for sectioning with a microtome and for subsequent microscopic investigation of the sections, provision can advantageously be made that the samples are each aligned relative to their casting mold in a target position in which the samples are to be immobilized, and are secured with a securing element in that target position during embedding. The automated embedding machine is in this regard preferably embodied to be used with a casting mold that comprises at least one securing element for physically securing a sample in a target position within the casting mold. For example, the sample can be clamped between the securing element and the bottom of the casting mold in order to secure the sample in the target position.

The casting mold can be embodied in particular in such a way that it can also function as a cassette, so that the histological processing operations that precede embedding, such as fixing and/or infiltration, can be performed on the position sample secured in a target position in the casting mold. The preceding operations can in particular be accomplished by a different automated machine.

The securing element can comprise, for example, a clamping means for clamping at least one sample. The clamping means can be embodied, for example, as a spring-loaded screen.

In order to allow sectioning of the block, once produced, with a microtome with no risk of damaging the microtome knife on the securing element, in a very particularly advantageous embodiment the securing element is removed from the sample during the cooling operation. This can be accomplished in particular by firstly cooling and thereby solidifying the embedding medium, in particular in a locally delimited manner within the casting mold, sufficiently that the sample is held in its position by the already solidified parts of the embedding medium, and then removing the securing element from the sample during the further cooling process.

An embodiment in which the securing element is removed from the sample by magnetic force is particularly advantageous, since no additional mechanical tools that must engage into the casting mold in order to remove the securing element are required. Removal of the securing element can instead occur in an advantageously noncontact manner, thereby avoiding the risk of damaging the sample or inadvertently modifying the orientation of the sample.

The securing element can be embodied as a magnet and/or can contain ferromagnetic particles. It is also possible, however, for the securing element to be embodied in at least partially paramagnetic fashion, and for the cooling station to comprise a preferably controllable magnet with which a force can be exerted on the securing element.

BRIEF DESCRIPTION OF THE DRAWING FIGURES

Figure 2:
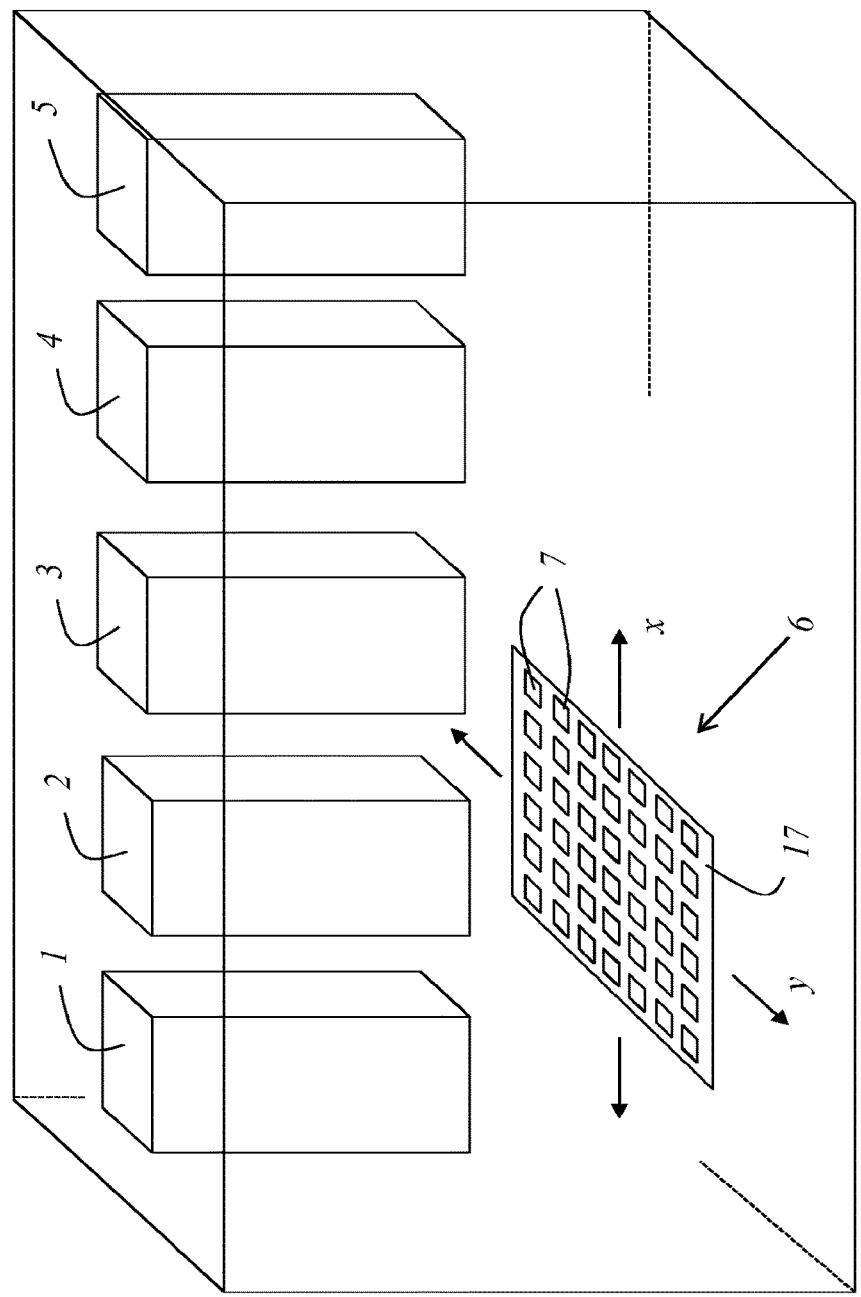

The subject matter of the invention is schematically depicted in the drawings and will be described below with reference to the Figures, identical or identically functioning elements for the most part being provided with the same reference characters. In the drawings:

FIG. 1 depicts an exemplifying embodiment of an automated embedding machine according to the present invention; and FIG. 2 depicts another exemplifying embodiment of an automated embedding machine according to the present invention.

DETAILED DESCRIPTION OF THE INVENTION

FIG. 1 schematically shows an exemplifying embodiment of an automated embedding machine according to the present invention that comprises a loading station 1, a pouring station 2, a cooling station 3, an identification station 4, and an unloading station 5. The automated embedding machine furthermore comprises a conveyor 6 that is embodied and arranged to receive casting molds 7 each having at least one histological sample 8 arranged therein, and to transport them further.

In order to ensure that sample 8 has, within the block to be produced, an alignment that is favorable for further processing, the samples are each aligned relative to their casting mold 7 in a target position in which the samples are to be block-embedded, and are secured in that target position with a securing element 12 that can be embodied e.g. as a screen-shaped clamping element. Sample 8 can be clamped in place, for example, between the clamping element and the bottom of casting mold 7.

Conveyor 6 transports casting molds 7 from loading station 1 firstly to pouring station 2, where each casting mold 7 is filled with an embedding medium 9, for example paraffin, heated to above its melting point. The liquid embedding medium 9 is taken from a reservoir container 10 and delivered in the correct amount, under automatic control, through a dispenser nozzle 11 into the respective casting mold 7.

After pouring at pouring station 2, casting molds 7 are transported on by conveyor 6 to cooling station 3, which contains a cooling apparatus 13. Here the embedding medium 9 delivered into the individual casting molds 7 is cooled to below its melting point.

During the cooling operation, the following effect is utilized: in the first moments of cooling, the lowest layer of the embedding medium present in casting mold 7 becomes solidified. Because sample 8 abuts directly against the bottom of casting mold 7, sample 8 is thereby secured by the solidifying embedding medium 9 in its target position, in which it has been held until then by securing element 12.

Because sample 8 is in contact on its upper side with securing element 12, which must not be cut into later by the microtome knife, said securing element 12 is then lifted in such a way that a spacing of, for example, 1 to 2 mm is created between the sample and securing element 12. As soon as lifting has occurred, the remaining embedding medium 9 in casting mold 7 can harden.

Lifting is accomplished with the aid of a magnet 14, preferably automatically controlled, that exerts a magnetic force on securing element 12, which can itself be magnetic or can contain magnetic particles. Another possibility for lifting is to lift securing element 12 using lever apparatuses or other mechanical means.

After cooling, the casting molds are transported by conveyor 6 from cooling station 3 to identification station 4, where an identifier 15 receives and/or reads off a respective specific code for each casting mold 7 and/or for the sample present therein and/or for each block that has been produced.

Identifier 15 forwards the information regarding the identified casting mold 7 to an information output interface 16, which is embodied to transmit the information to a laboratory information system and/or to a local output means, for example to a display screen or a printer.

After the identification operation, casting molds 7 are further transported by conveyor 6 to unloading station 5, which is embodied as an unloading buffer. The completed casting molds 7 having the completed blocks can be removed automatically or manually from unloading station 5. The hardened blocks are taken out of casting molds 7 for further processing.

FIG. 2 shows another exemplifying embodiment of an automated embedding machine according to the present invention that likewise contains a loading station 1, a pouring station 2, a cooling station 3, an identification station 4, an unloading station 5, and a conveyor 6.

In this automated embedding machine, conveyor 6 comprises a holder 17 for multiple casting molds 7 which is movable relative to stations 2, 3, 4, 5, and which is moved by a control apparatus in such a way that each of the casting molds 7 held by holder 17 travels successively to each of stations 2, 3, 4, 5. For example, a displacement stage can be present with which holder 7 can be displaced in two or three dimensions.

PARTS LIST

1 Loading station
2 Pouring station
3 Cooling station
4 Identification station
5 Unloading station
6 Conveyor
7 Casting molds
8 Sample
9 Embedding medium
10 Reservoir container
11 Dispenser nozzle
12 Securing element
13 Cooling apparatus
14 Magnet
15 Identifier
16 Information output interface
17 Holder

What is claimed is:

1. A method for embedding histological samples, comprising the steps of:
   a. inserting histological samples into casting molds, at least one of the histological samples being inserted into one of the casting molds, wherein the samples are each aligned relative to the respective casting mold in a target position in which the samples are to be block-embedded, and are secured in the target position with a securing element;
   b. transferring the casting molds having the samples to a loading station of an automated embedding machine, the automated embedding machine further comprising a conveyor, a pouring station, and a cooling station, wherein the loading station is embodied as a loading buffer configured to hold a plurality of the casting molds;
   c. conveying the transferred casting molds, using the conveyor, to the pouring station that fills each of the casting molds with an embedding medium heated to above a melting point of the embedding medium; and
   d. conveying the casting molds, filled with the embedding medium, to the cooling station that cools the embedding medium of each of the casting molds to below the melting point of the embedding medium, wherein the securing element is removed from the sample while the embedding medium is cooled.

2. The method according to claim 1, wherein the securing element is removed from the sample by magnetic force.

3. The method according to claim 1, wherein the automated embedding machine comprises at least one further station, and the casting molds are transported by the conveyor to the further station.

4. The method according to claim 1, wherein the conveyor receives the casting molds for further transport from the loading station.

5. The method according to claim 1, further comprising the step of identifying each of the casting molds and/or the at least one sample present therein and/or each solidified block by reading or receiving a specific code associated with the casting mold and/or the at least one sample and/or the solidified block.

6. The method according to claim 5, further comprising the step of outputting an information item about each of the casting molds and/or the at least one sample present therein and/or each solidified block to a laboratory information system.

7. The method according to claim 1, wherein the casting molds are transported in a continuous transport stream along a predefined conveying path.

8. The method according to claim 1, wherein the casting molds are transported individually along a predefined transport path.

9. The method according to claim 1, wherein the casting molds are transported in groups along a predefined conveying path.

10. The method according to claim 9, wherein the casting molds of each of the groups are secured in a shared holder.

11. The method according to claim 1, wherein the conveyor comprises a holder for multiple casting molds, the holder being movable relative to the loading, pouring, and cooling stations by a control apparatus such that each of the casting molds held by the holder travels successively to each of the loading, pouring, and cooling stations.

12. The method according to claim 11, wherein the conveying path is identical for all the casting molds.

13. The method according to claim 1, further comprising transporting the casting molds having the cooled embedding medium by the conveyor to an unloading station of the automated embedding machine, wherein the unloading station is embodied as an unloading buffer configured to hold a plurality of the casting molds.

* * * * *